(12) United States Patent
Coley et al.

(10) Patent No.: US 9,205,257 B1
(45) Date of Patent: Dec. 8, 2015

(54) METHOD AND APPARATUS FOR INDUCING THE PERCEPTION OF COLOR IN A VISUAL PROSTHESIS

(75) Inventors: Brian Coley, Vufflens-la-ville (CH); Francesco Merlini, Renes (CH); Robert J. Greenberg, Los Angeles, CA (US)

(73) Assignee: Second Sight Medical Products, Inc., Sylmar, CA (US)

(*) Notice: Subject to any disclaimer, the term of this patent is extended or adjusted under 35 U.S.C. 154(b) by 0 days.

(21) Appl. No.: 13/481,425

(22) Filed: May 25, 2012

Related U.S. Application Data

(60) Provisional application No. 61/490,468, filed on May 26, 2011.

(51) Int. Cl.
*A61N 1/32* (2006.01)
*A61N 1/36* (2006.01)
*A61F 2/14* (2006.01)

(52) U.S. Cl.
CPC ............ *A61N 1/36046* (2013.01); *A61F 2/141* (2013.01); *A61F 2/145* (2013.01)

(58) Field of Classification Search
CPC .... A61N 1/36046; A61N 2/141; A61N 2/145
USPC .................... 607/54, 53; 623/6.63
See application file for complete search history.

(56) References Cited

U.S. PATENT DOCUMENTS

| | | |
|---|---|---|
| 4,573,481 A | 3/1986 | Bullara |
| 4,628,933 A | 12/1986 | Michelson |
| 4,837,049 A | 6/1989 | Byers et al. |
| 5,109,844 A | 5/1992 | de Juan, Jr. et al. |
| 5,215,088 A | 6/1993 | Normann et al. |
| 5,935,155 A | 8/1999 | Humayun et al. |
| 6,400,989 B1 | 6/2002 | Eckmiller |
| 6,458,157 B1 * | 10/2002 | Suaning ............... A61N 1/0543 623/6.63 |
| 7,257,446 B2 * | 8/2007 | Greenberg et al. .. A61N 1/0543 607/54 |

* cited by examiner

*Primary Examiner* — Theodore Stigell
*Assistant Examiner* — Michael Carey
(74) *Attorney, Agent, or Firm* — Scott B. Dunbar

(57) ABSTRACT

The present invention is an improved method of electrically stimulating percepts in a patient with a visual prosthesis, to induce the perception of color. In particular, the present invention is a method of inducing the perception of color by determining experimentally which patterns induce which colors, storing that information and using the stored information to induce the perception of color according to video input data and the stored color information.

15 Claims, 19 Drawing Sheets

METHOD AND APPARATUS FOR INDUCING THE PERCEPTION OF COLOR IN A VISUAL PROSTHESIS

CROSS REFERENCE TO RELATED APPLICATIONS

The present application claims priority to U.S. Provisional Application No. 61/490,468 entitled "Method and Apparatus for Inducing Perception of Color in a Visual Prosthesis", filed on May 26, 2011, which is incorporated herein by reference in its entirety.

FIELD OF THE INVENTION

The present invention is generally directed to neural stimulation and more specifically to an improved method of controlling color perception in a visual prosthesis.

BACKGROUND OF THE INVENTION

In 1755 LeRoy passed the discharge of a Leyden jar through the orbit of a man who was blind from cataract and the patient saw "flames passing rapidly downwards." Ever since, there has been a fascination with electrically elicited visual perception. The general concept of electrical stimulation of retinal cells to produce these flashes of light or phosphenes has been known for quite some time. Based on these general principles, some early attempts at devising prostheses for aiding the visually impaired have included attaching electrodes to the head or eyelids of patients. While some of these early attempts met with some limited success, these early prosthetic devices were large, bulky and could not produce adequate simulated vision to truly aid the visually impaired.

In the early 1930's, Foerster investigated the effect of electrically stimulating the exposed occipital pole of one cerebral hemisphere. He found that, when a point at the extreme occipital pole was stimulated, the patient perceived a small spot of light directly in front and motionless (a phosphene). Subsequently, Brindley and Lewin (1968) thoroughly studied electrical stimulation of the human occipital (visual) cortex. By varying the stimulation parameters, these investigators described in detail the location of the phosphenes produced relative to the specific region of the occipital cortex stimulated. These experiments demonstrated: (1) the consistent shape and position of phosphenes; (2) that increased stimulation pulse duration made phosphenes brighter; and (3) that there was no detectable interaction between neighboring electrodes which were as close as 2.4 mm apart.

As intraocular surgical techniques have advanced, it has become possible to apply stimulation on small groups and even on individual retinal cells to generate focused phosphenes through devices implanted within the eye itself. This has sparked renewed interest in developing methods and apparati to aid the visually impaired. Specifically, great effort has been expended in the area of intraocular retinal prosthesis devices in an effort to restore vision in cases where blindness is caused by photoreceptor degenerative retinal diseases; such as retinitis pigmentosa and age related macular degeneration which affect millions of people worldwide.

Present studies have been performed on use of retinal prostheses to restore partial sight to people blinded by outer retinal degenerative diseases. Diseases such as retinitis pigmentosa destroy photoreceptors but leave a significant percentage of inner-retinal cells (ganglion and bipolar cells) intact and functional. Direct electrical stimulation of inner-retinal cells via an implanted array of electrodes may provide vision.

Neural tissue can be artificially stimulated and activated by prosthetic devices that pass pulses of electrical current through electrodes on such a device. The passage of current causes changes in electrical potentials across visual neuronal membranes, which can initiate visual neuron action potentials, which are the means of information transfer in the nervous system.

Based on this mechanism, it is possible to input information into the nervous system by coding the sensory information as a sequence of electrical pulses which are relayed to the nervous system via the prosthetic device. In this way, it is possible to provide artificial sensations including vision.

One typical application of neural tissue stimulation is in the rehabilitation of the blind. Some forms of blindness involve selective loss of the light sensitive transducers of the retina. Other retinal neurons remain viable, however, and may be activated in the manner described above by placement of a prosthetic electrode device on the inner (toward the vitreous) retinal surface (epiretinal). This placement must be mechanically stable, minimize the distance between the device electrodes and the visual neurons, control the electronic field distribution and avoid undue compression of the visual neurons.

In 1986, Bullara (U.S. Pat. No. 4,573,481) patented an electrode assembly for surgical implantation on a nerve. The matrix was silicone with embedded iridium electrodes. The assembly fit around a nerve to stimulate it.

Dawson and Radtke stimulated cat's retina by direct electrical stimulation of the retinal ganglion cell layer. These experimenters placed nine and then fourteen electrodes upon the inner retinal layer (i.e., primarily the ganglion cell layer) of two cats. Their experiments suggested that electrical stimulation of the retina with 30 to 100 µA current resulted in visual cortical responses. These experiments were carried out with needle-shaped electrodes that penetrated the surface of the retina (see also U.S. Pat. No. 4,628,933 to Michelson).

The Michelson '933 apparatus includes an array of photosensitive devices on its surface that are connected to a plurality of electrodes positioned on the opposite surface of the device to stimulate the retina. These electrodes are disposed to form an array similar to a "bed of nails" having conductors which impinge directly on the retina to stimulate the retinal cells. U.S. Pat. No. 4,837,049 to Byers describes spike electrodes for neural stimulation. Each spike electrode pierces neural tissue for better electrical contact. U.S. Pat. No. 5,215,088 to Norman describes an array of spike electrodes for cortical stimulation. Each spike pierces cortical tissue for better electrical contact.

The art of implanting an intraocular prosthetic device to electrically stimulate the retina was advanced with the introduction of retinal tacks in retinal surgery. De Juan, et al. at Duke University Eye Center inserted retinal tacks into retinas in an effort to reattach retinas that had detached from the underlying choroid, which is the source of blood supply for the outer retina and thus the photoreceptors. See, e.g., E. de Juan, et al., 99 Am. J. Ophthalmol. 272 (1985). These retinal tacks have proved to be biocompatible and remain embedded in the retina, and choroid/sclera, effectively pinning the retina against the choroid and the posterior aspects of the globe. Retinal tacks are one way to attach a retinal electrode array to the retina. U.S. Pat. No. 5,109,844 to de Juan describes a flat electrode array placed against the retina for visual stimulation. U.S. Pat. No. 5,935,155 to Humayun describes a retinal prosthesis for use with the flat retinal array described in de Juan. U.S. Pat. No. 7,257,446 describes generally the process of stimulating the perception of color by altering frequency and pulse width.

Color perception in a normally sighted person is caused by specialized cone cells which are sensitive to different frequency light. In outer retinal degenerative diseases, such as retinitis pigmentosa or age related macular degeneration, the cones to do not function. Further, the cone cells are too small to stimulate individually. The stimulation patters of these cone cells varies from one individual to another and from one area of the retina to another.

SUMMARY OF THE INVENTION

The present invention is an improved method of electrically stimulating percepts in a patient with a visual prosthesis, to induce the perception of color. In particular, the present invention is a method of inducing the perception of color by determining experimentally which patterns induce which colors, storing that information and using the stored information to induce the perception of color according to video input data and the stored color information. The parameters mapped to color are current, frequency, pulse width, inter-pulse gap, an electrode or electrode group. The process is similar to brightness fitting which is well known. Tissue response differently to intensity of stimulation a visual prosthesis must map brightness of an input image to varying intensity of stimulation. This can be carried to the next step to fit color as well.

According to a first aspect of the disclosure, a method of inducing perception of color with a visual prosthesis is provided, comprising: testing stimulation patterns on one or more subjects; determining which stimulation patterns include which color; storing relationships of stimulation patterns and colors; and using the stored relationships to determine patterns used for later stimulation According to a second aspect of the disclosure, a visual prosthesis is provided, comprising: a camera providing video data to a video processing unit; the video processing unit including memory means for storing individual color video configuration information and processing means for altering the video data according to the stored color video configuration information; and a neural stimulation receiving video data from the video processing unit and stimulating visual neurons according to video data altered according to the color video configuration information.

According to a third aspect of the disclosure, a method of inducing perception of a particular color with a visual prosthesis is provided, the visual prosthesis comprising an array of electrodes for stimulating an eye of a subject, the method comprising: testing stimulation patterns on the subject by applying stimulation signals to the subject through the array of electrodes; determining whether the subject perceives the particular color in the stimulation patterns; and adjusting at least one of frequency, pulse width, inter-pulse gap, and intra-pulse gap of the stimulation signals based on the determining.

Further embodiments are shown in the specification, drawings, and claims of the present application.

BRIEF DESCRIPTION OF THE DRAWINGS

The accompanying drawings, which are incorporated into and constitute a part of this specification, illustrate one or more embodiments of the present disclosure and, together with the description of example embodiments, serve to explain the principles and implementations of the disclosure.

DETAILED DESCRIPTION OF THE PREFERRED EMBODIMENTS

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
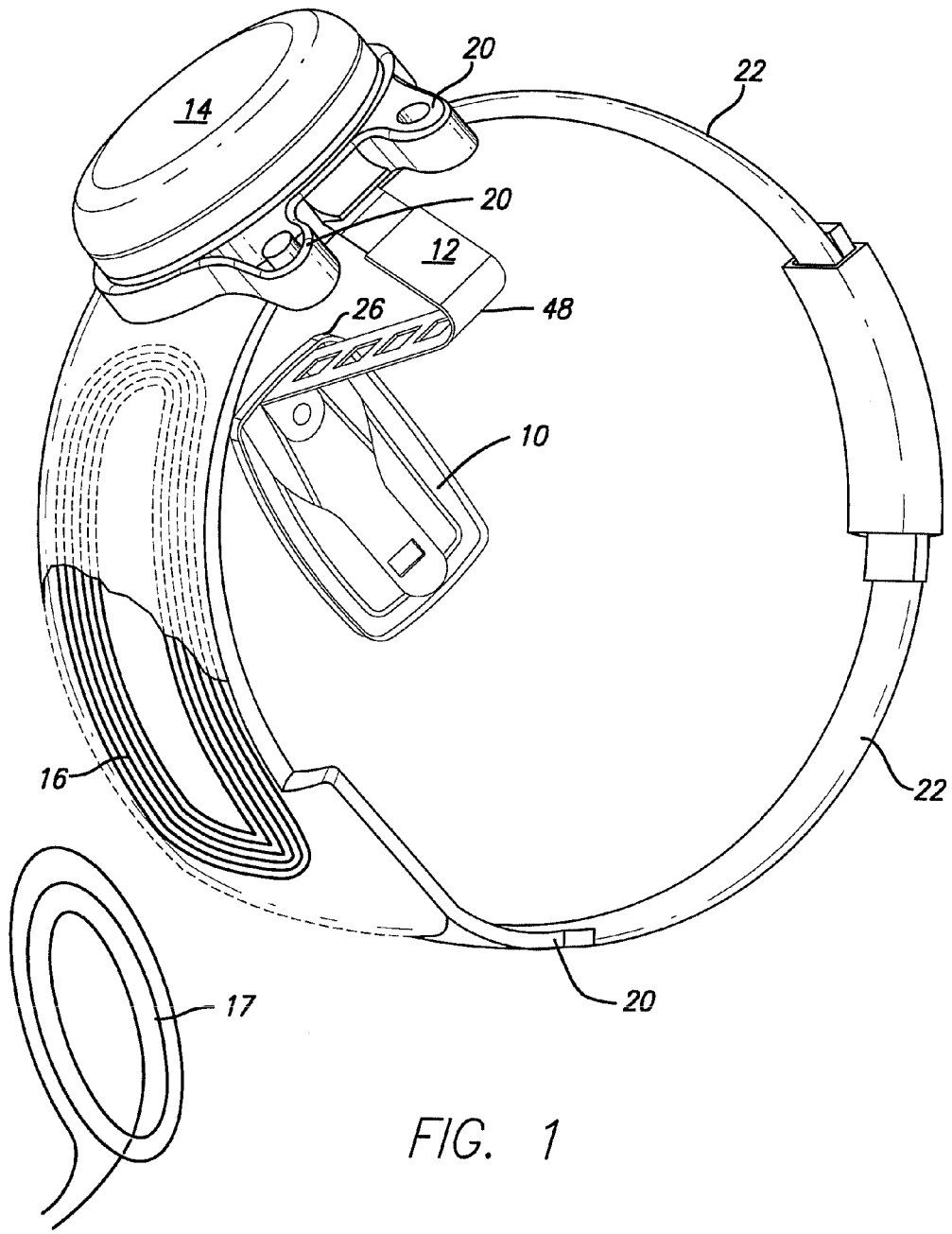
FIG. 1 is a perspective view of the implanted portion of the preferred retinal prosthesis.
Figure 2:
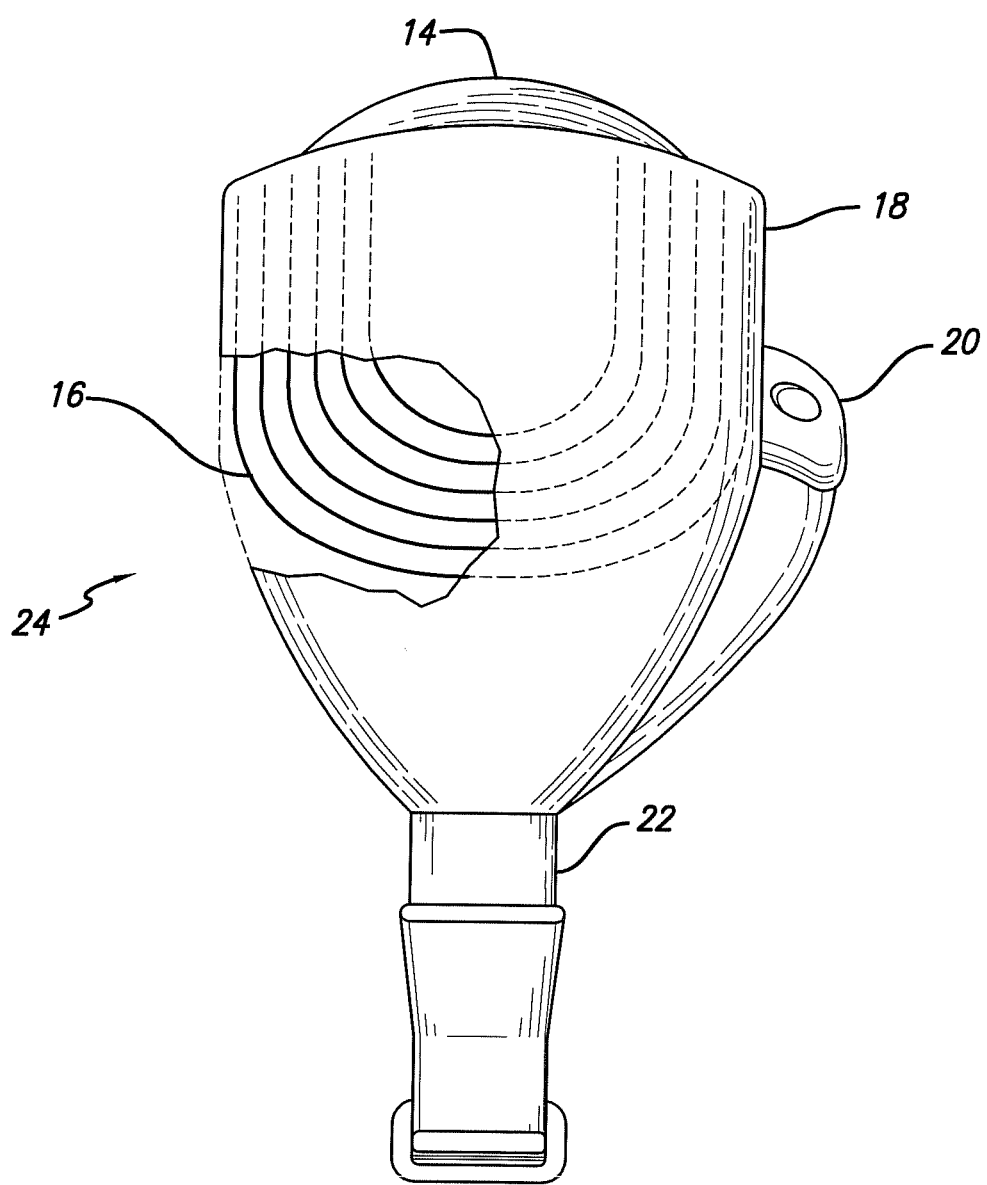
FIG. 2 is a side view of the implanted portion of the preferred retinal prosthesis showing the strap fan tail in more detail.

FIGS. 1 and 2 present the general structure of a visual prosthesis used in implementing the invention.

FIG. 1 shows a perspective view of the implanted portion of the preferred retinal prosthesis. A flexible circuit 1 includes a flexible circuit electrode array 10 which is mounted by a retinal tack (not shown) or similar means to the epiretinal surface. The flexible circuit electrode array 10 is electrically coupled by a flexible circuit cable 12, which pierces the sclera and is electrically coupled to an electronics package 14, external to the sclera.

The electronics package 14 is electrically coupled to a secondary inductive coil 16. Preferably the secondary inductive coil 16 is made from wound wire. Alternatively, the secondary inductive coil 16 may be made from a flexible circuit polymer sandwich with wire traces deposited between layers of flexible circuit polymer. The secondary inductive coil receives power and data from a primary inductive coil 17, which is external to the body. The electronics package 14 and secondary inductive coil 16 are held together by the molded body 18. The molded body 18 holds the electronics package 14 and secondary inductive coil 16 end to end. The secondary inductive coil 16 is placed around the electronics package 14 in the molded body 18. The molded body 18 holds the secondary inductive coil 16 and electronics package 14 in the end to end orientation and minimizes the thickness or height above the sclera of the entire device. The molded body 18 may also include suture tabs 20. The molded body 18 narrows to form a strap 22 which surrounds the sclera and holds the molded body 18, secondary inductive coil 16, and electronics package 14 in place. The molded body 18, suture tabs 20 and strap 22 are preferably an integrated unit made of silicone elastomer. Silicone elastomer can be formed in a pre-curved shape to match the curvature of a typical sclera. However, silicone remains flexible enough to accommodate implantation and to adapt to variations in the curvature of an individual sclera. The secondary inductive coil 16 and molded body 18 are preferably oval shaped. A strap 22 can better support an oval shaped coil. It should be noted that the entire implant is attached to and supported by the sclera. An eye moves constantly. The eye moves to scan a scene and also has a jitter motion to improve acuity. Even though such motion is useless in the blind, it often continues long after a person has lost their sight. By placing the device under the rectus muscles with the electronics package in an area of fatty tissue between the rectus muscles, eye motion does not cause any flexing which might fatigue, and eventually damage, the device.

FIG. 2 shows a side view of the implanted portion of the retinal prosthesis, in particular, emphasizing the fan tail 24. When implanting the retinal prosthesis, it is necessary to pass the strap 22 under the eye muscles to surround the sclera. The secondary inductive coil 16 and molded body 18 must also follow the strap 22 under the lateral rectus muscle on the side of the sclera. The implanted portion of the retinal prosthesis is very delicate. It is easy to tear the molded body 18 or break wires in the secondary inductive coil 16. In order to allow the molded body 18 to slide smoothly under the lateral rectus muscle, the molded body 18 is shaped in the form of a fan tail 24 on the end opposite the electronics package 14. The strap 22 further includes a hook 28 the aids the surgeon in passing the strap under the rectus muscles.

Figure 3:
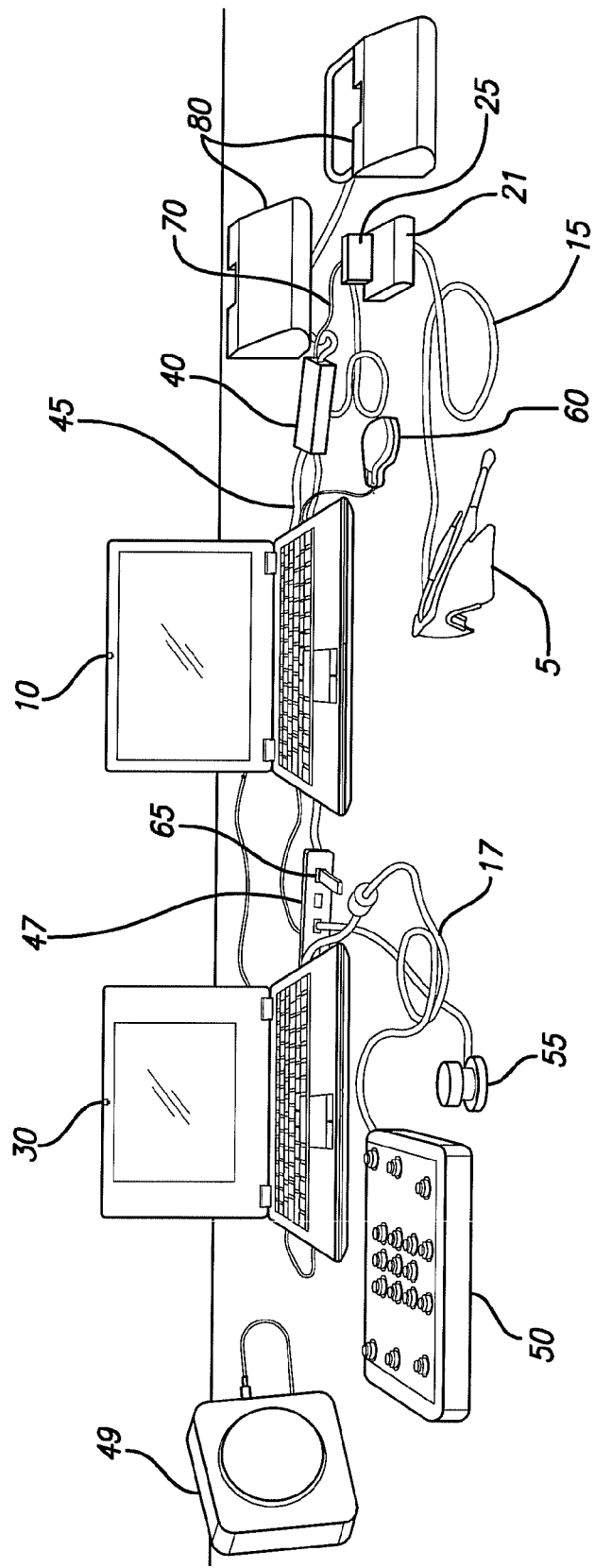
FIG. 3 shows the components of a visual prosthesis fitting system.

Referring to FIG. 3, a Fitting System (FS) may be used to configure and optimize the visual prosthesis (3) of the Retinal Stimulation System (1).

The Fitting System may comprise custom software with a graphical user interface (GUI) running on a dedicated laptop computer (10). Within the Fitting System are modules for performing diagnostic checks of the implant, loading and executing video configuration files, viewing electrode voltage waveforms, and aiding in conducting psychophysical experiments. A video module can be used to download a video configuration file to a Video Processing Unit (VPU) (20) and store it in non-volatile memory to control various aspects of video configuration, e.g. the spatial relationship between the video input and the electrodes. The software can also load a previously used video configuration file from the VPU (20) for adjustment.

The Fitting System can be connected to the Psychophysical Test System (PTS), located for example on a dedicated laptop (30), in order to run psychophysical experiments. In psychophysics mode, the Fitting System enables individual electrode control, permitting clinicians to construct test stimuli with control over current amplitude, pulse-width, and frequency of the stimulation. In addition, the psychophysics module allows the clinician to record subject responses. The PTS may include a collection of standard psychophysics experiments developed using for example MATLAB (MathWorks) software and other tools to allow the clinicians to develop customized psychophysics experiment scripts.

Any time stimulation is sent to the VPU (20), the stimulation parameters are checked to ensure that maximum charge per phase limits, charge balance, and power limitations are met before the test stimuli are sent to the VPU (20) to make certain that stimulation is safe.

Using the psychophysics module, important perceptual parameters such as perceptual threshold, maximum comfort level, and spatial location of percepts may be reliably measured.

Based on these perceptual parameters, the fitting software enables custom configuration of the transformation between video image and spatio-temporal electrode stimulation parameters in an effort to optimize the effectiveness of the retinal prosthesis for each subject.

The Fitting System laptop (10) is connected to the VPU (20) using an optically isolated serial connection adapter (40). Because it is optically isolated, the serial connection adapter (40) assures that no electric leakage current can flow from the Fitting System laptop (10).

As shown in FIG. 3, the following components may be used with the Fitting System according to the present disclosure. A Video Processing Unit (VPU) (20) for the subject being tested, a Charged Battery (25) for VPU (20), Glasses (5), a Fitting System (FS) Laptop (10), a Psychophysical Test System (PTS) Laptop (30), a PTS CD (not shown), a Communication Adapter (CA) (40), a USB Drive (Security) (not shown), a USB Drive (Transfer) (not shown), a USB Drive (Video Settings) (not shown), a Patient Input Device (RF Tablet) (50), a further Patient Input Device (Jog Dial) (55), Glasses Cable (15), CA-VPU Cable (70), CFS-CA Cable (45), CFS-PTS Cable (46), Four (4) Port USB Hub (47), Mouse (60), LED Test Array (80), Archival USB Drive (49), an Isolation Transformer (not shown), adapter cables (not shown), and an External Monitor (not shown).

The external components of the Fitting System according to the present disclosure may be configured as follows. The battery (25) is connected with the VPU (20). The PTS Laptop (30) is connected to FS Laptop (10) using the CFS-PTS Cable (46). The PTS Laptop (30) and FS Laptop (10) are plugged into the Isolation Transformer (not shown) using the Adapter Cables (not shown). The Isolation Transformer is plugged into the wall outlet. The four (4) Port USB Hub (47) is connected to the FS laptop (10) at the USB port. The mouse (60) and the two Patient Input Devices (50) and (55) are connected to four (4) Port USB Hubs (47). The FS laptop (10) is connected to the Communication Adapter (CA) (40) using the CFS-CA Cable (45). The CA (40) is connected to the VPU (20) using the CA-VPU Cable (70). Glasses (5) are connected to the VPU (20) using the Glasses Cable (15).

Figure 5:
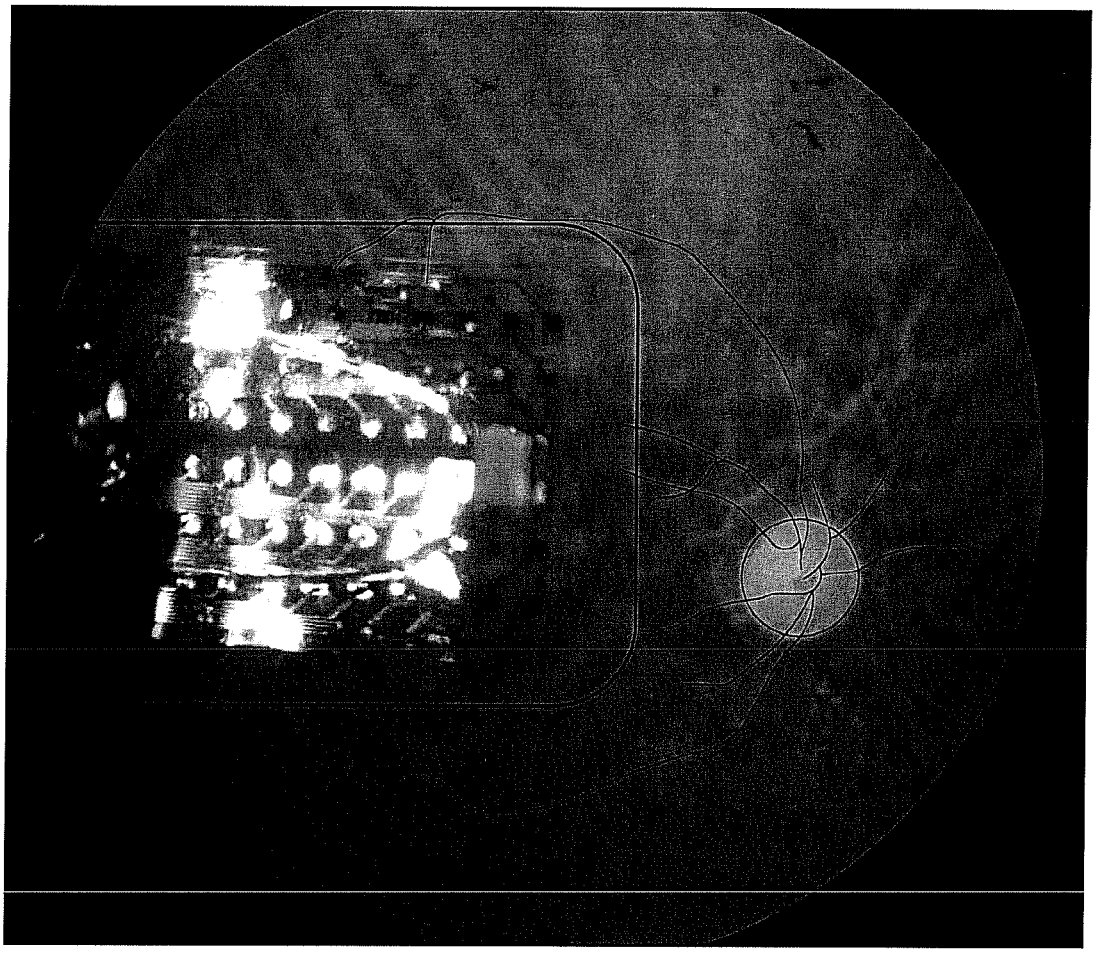
FIG. 5 shows an epiretinal prosthesis tacked onto the macula of the retina.

FIG. 5 shows an epiretinal prosthesis tacked onto the macula of the retina.

Figure 6A:
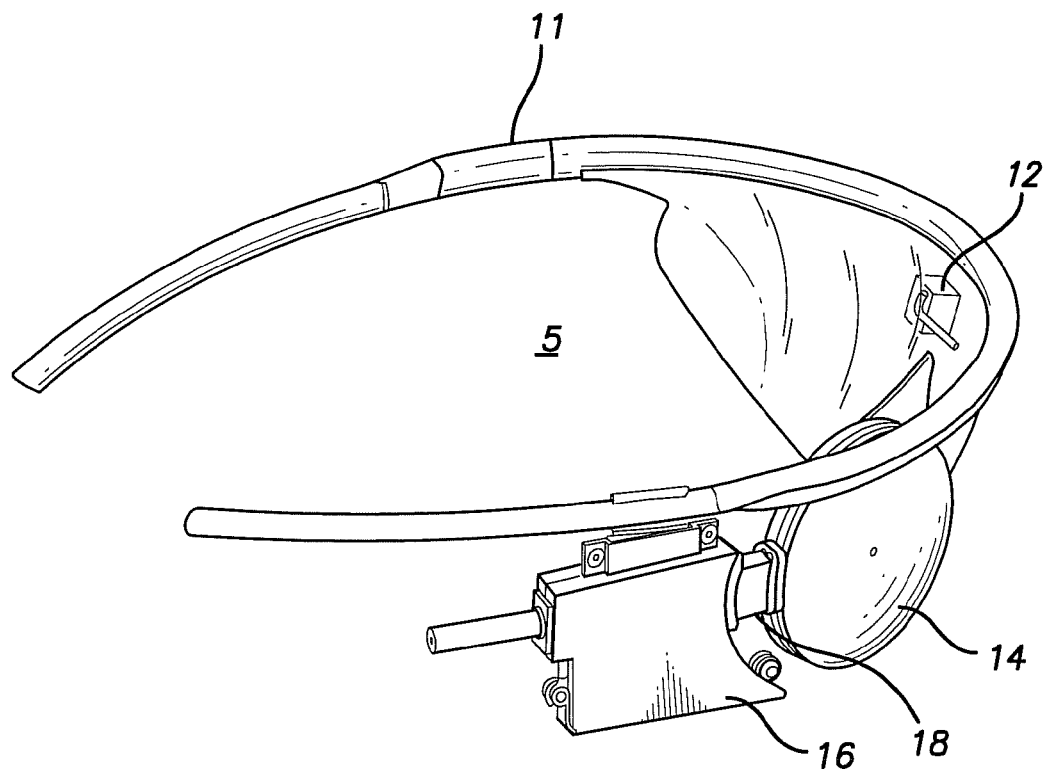
FIG. 6A shows a side view of an exemplary pair of glasses for capturing and transmitting video information.
Figure 6B:
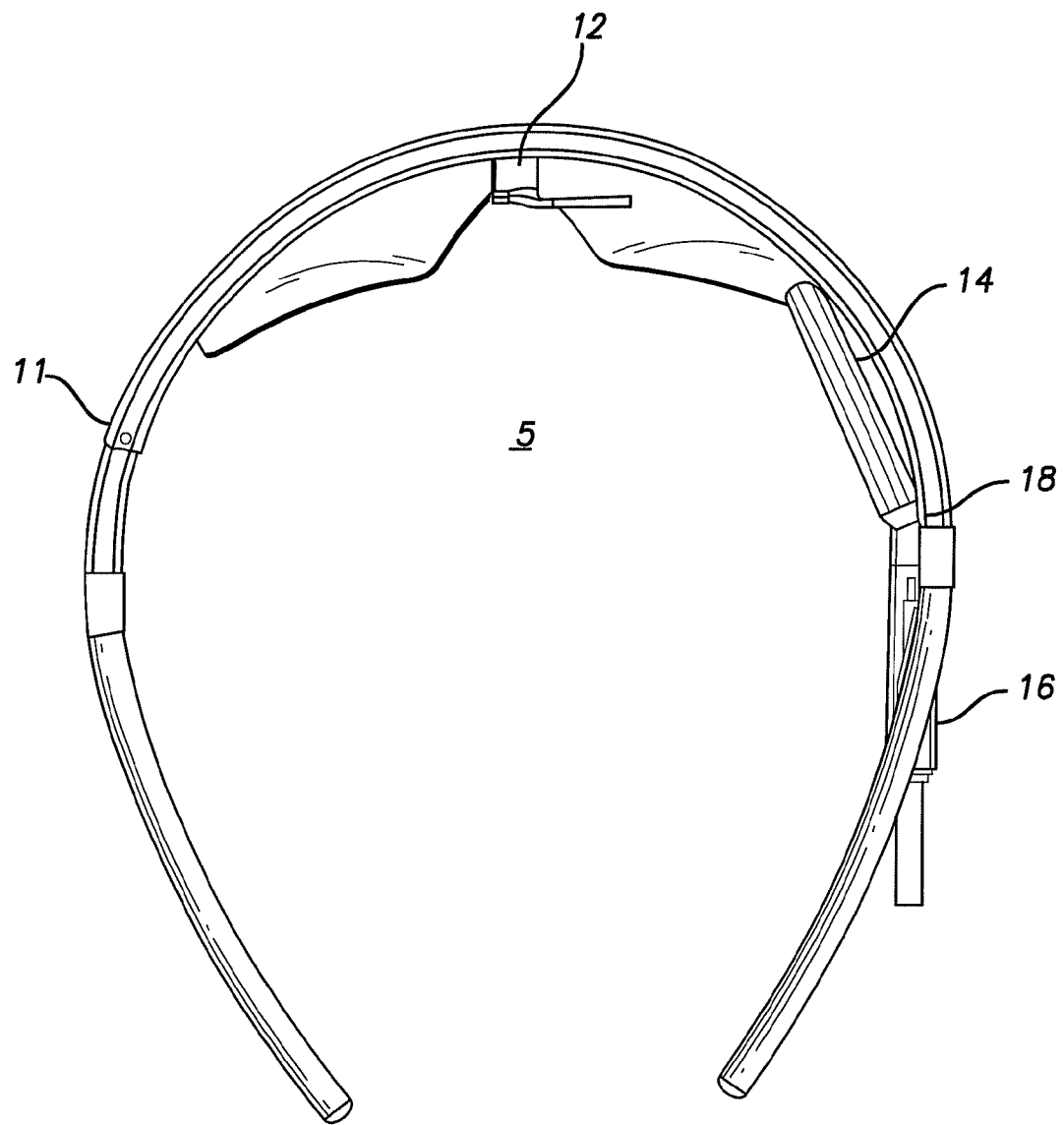
FIG. 6B shows a top view of the exemplary pair of glasses shown in FIG. 6A.
Figure 6C:
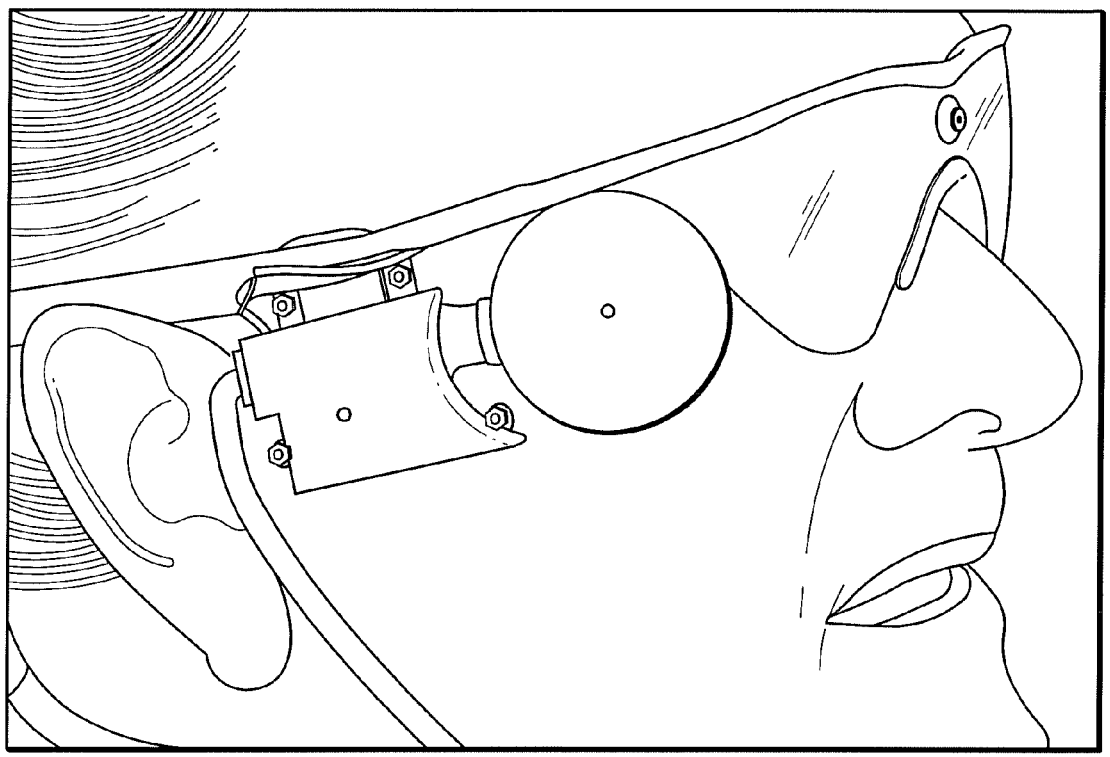
FIG. 6C shows a subject wearing the exemplary pair of glasses.

FIG. 6A shows a side view of an exemplary pair of glasses 5 for capturing and transmitting video information. The pair of glasses 5 can comprise, for example, a frame 11 for holding a video camera 12, an external coil 14, and a mounting system 16 for the external coil 14. The mounting system 16 may also enclose the RF circuitry. In this configuration, the video camera 12 captures live video. The video signal can be sent, for instance, to an external VPU 20 shown in FIG. 3, which processes the video signal and subsequently transforms the processed video signal into electrical stimulation patterns or data. The electrical stimulation data are then sent to the external coil 14 which sends both the data and power via radio-frequency (RF) telemetry to an implanted portion of the retinal prosthesis (such as a receiving coil in the retinal prosthesis) and/or an external testing unit for testing/measuring of the data and power received from the external coil 14. FIG. 6B shows a top view of the exemplary pair of glasses while FIG. 6C shows a subject wearing the exemplary pair of glasses.

Video Configuration Information

Video processing can be configured using a collection of settings known as video configuration information. This information can be dynamically set by the host. It includes a spatial map, a brightness map color map, timing profiles, and Image Presentation Rate/Stimulation Frequency and zoom settings.

The spatial map is used by the video filters when processing the raw video image. The spatial map can contain one pixel location for every electrode and assume a 12×20 raw video image. A possible application programming interface (API) can be defined as follows:

```
# define ELECTRODE_NUM (60)
typedef struct {
unsigned short columnPosition; //column 0-19
unsigned short rowPosition; //row 0-11
} pixelCnordinate;
pixelCoordinate spatialMap[ELECTRODE_NUM];
```

The brightness map is used by the telemetry engine video manager (140), later discussed, to translate the filtered video image brightness levels to driver amplitude values. For each brightness level, an electrode can have a unique corresponding driver amplitude value. There can be one driver amplitude range that is used for all electrodes.

```
# define BRIGHTNESS_LEVELS
    unsigned short brightnessMap[ELECTRODE_NUM]
[BRIGHTNESS_LEVELS];
    unsigned short globalAmplitudeRange;
```

According to one embodiment of the present disclosure, there are six timing profiles that can be configured. Each electrode associates one of the six profiles with its anodic pulse, and one of the six for its cathodic pulse.

```
# define PROFILE_NUM
typedef struct {
unsigned short start;
unsigned short stop;
} profile;
profile timingProfiles[PROFILE_NUM];
typedef struct {
unsigned short anodicProfile;
unsigned short cathodicProfile;
} profileChoice;
    profileChoice electrodeProfileSelection[ELECTRODE_NUM];
```

As to the video filter settings, the filter processor can be configured to perform a reverse video filter in conjunction with the DoG filter.

```
struct {
int reverseVideoOn; //TRUE or FALSE}
```

Figure 4:
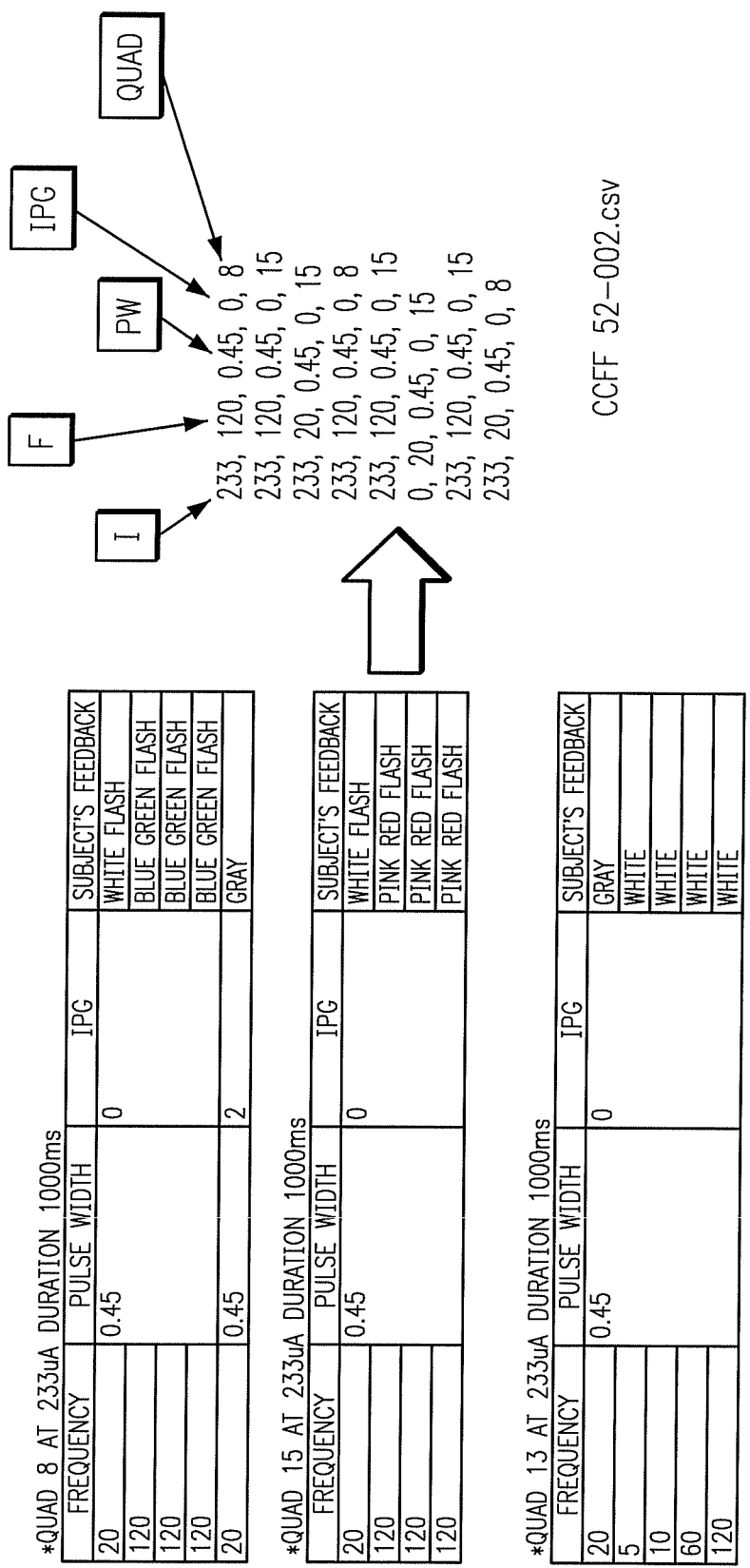
FIG. 4 is an example of a typical color stimulation map.

The Image Presentation Rate/Stimulation Frequency is used to determine how often to present a new video image to the patient. The maximum effective rate can be 30 Hz if a Phillips video decoder is used as decoder. The host specifies how many frames to pad between video image frames. It can be configured for faster than 30 Hz, but this means a video frame is repeated.

unsigned short imageFrequencyPadding;
[The zoom setting for the video image capture can be set via the keypad. unsigned short zoomSetting; //zoom in or zoom out FIG. 4 is an example of typical color configuration file. The patient is directly stimulated with a series of stimulation pulse and asked what color they see. Each stimulation pulse is defined as current, frequency, pulse width, inter-pulse gap and electrode or group of electrodes in this example. Each stimulation pulse is a biphasic cathodic first pulse. The inter-pulse gap is the time gap between the cathodic and anodic phase of the pulse. Once, a table of color the stimulation parameter is established, the software in the video processing unit can map colors to stimulation patterns providing color vision to the patient. The video signal is separated by chrominance or color information. Each color is mapped according to the stored color video configuration information.

Experimental Data

According to an embodiment of the present disclosure, a retinal prosthesis system comprises an array of electrodes implanted epiretinally, an inductive coil to wirelessly relay data and power to circuitry external to the eye, an external video processing unit (VPU) 20 (shown in FIG. 3), and a device for capturing and transmitting video signals.

In general for the implanted portion of the retinal prosthesis system, electronics can be sutured episcerally and then, after a vitrectomy surgery, the array of electrodes can be inserted through the pars plana and tacked to the retina in the macular region.

The device for capturing and transmitting video signals can be, for example, a video camera 12 (shown in FIGS. 6A-6B) that is mounted on a pair of glasses 5 (shown in FIGS. 3 and 6A-6C) suitable to be worn by a subject. The video camera 12 can capture the video signals in real time and transmit the video signals to the VPU 20. By way of example and not of limitation, the VPU 20 can perform one or more of digitizing the video signals, applying image-processing filters to the video signals, and downsampling resolution of the video signals to be suitable to the array of electrodes.

An exemplary retinal prosthesis system contains an array of sixty independently controlled electrodes implanted epiretinally. For instance, the array of electrodes can form a 6×10 grid of electrodes. In such a system, the video signal can be a sixty-pixel image or downsampled to a sixty-pixel image such that each pixel corresponds to one electrode. Each pixel in the sixty-pixel image is mapped to a stimulation amplitude to be applied to an electrode corresponding to the particular pixel. The mapping can be performed using look-up tables, which are generally customized for each subject. These customized look-up tables are built through experimental data obtained from each particular subject. The retinal prosthesis system contains memory for storage of the look-up table or tables obtained from experiments. Generally, the VPU 20 of the retinal prosthesis system contains memory for suitable for storage of these look-up table or tables.

The Applicants performed a study on subjects blinded by outer retinal dystrophies using the exemplary retinal prosthesis system with a 6×10 grid of electrodes. The subjects were tested to determine whether they can consistently perceive different colors in a video signal. The video camera of the retinal prosthesis system is suitable for recording color information.

Specifically, fourteen blind subjects with retinitis pigmentosa fitted with the exemplary retinal prosthesis system were tested. These subjects had bare light perception or worse vision in both eyes, functional ganglion cells and an intact optic nerve, and a confirmed history of useful form vision. The fitting of color for a retinal prosthesis system may occur (but need not occur) subsequent to fitting of the retinal prosthesis system for brightness perception. As used in this disclosure, the term "fitting" refers to calibration/customization of a retinal stimulation system, including the implanted electrodes, for each particular subject such that the retinal stimulation system allows for optimal or near optimal perception results for the particular subject.

Different groups of electrodes were stimulated with trains of cathodic-anodic pulses with different parameters. Specifically, pulses of various combinations of five different frequencies (5, 10, 20, 60, and 120 Hz), five different pulse widths (0.2 0.45, 0.6, 0.8, and 1 ms), and five different inter-pulse gaps (0, 1, 2, 3, and 4 ms) were utilized to stimulate the different groups of electrodes. The subjects reported the color they perceived after each stimulation.

Figure 7:
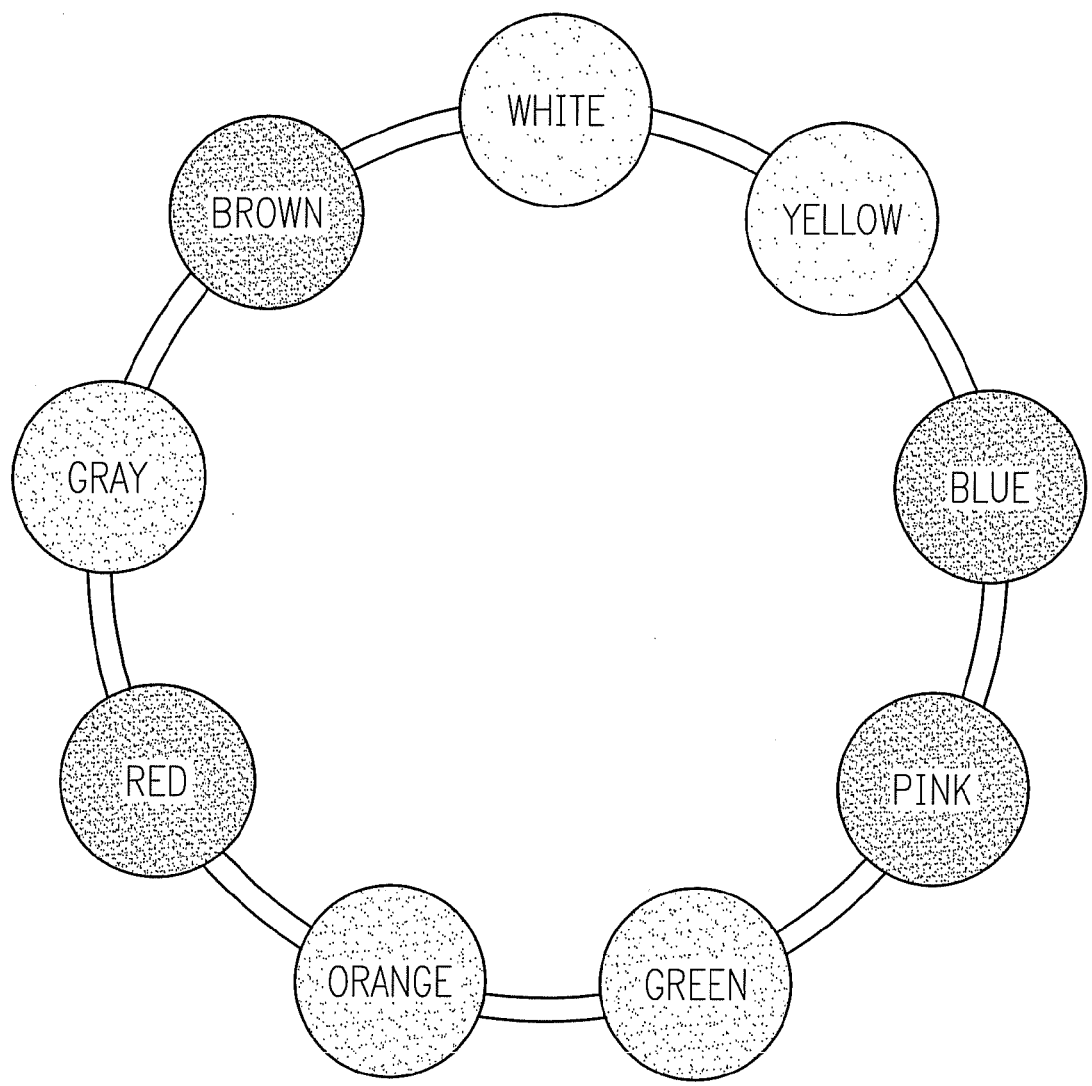
FIG. 7 shows colors that subjects of an experiment reported to perceive, where the experiment was conducted to determine whether the subjects can consistently perceive different colors in a video signal.

FIG. 7 shows colors that the subjects of an experiment reported to perceive, where the experiment was conducted to determine whether the subjects can consistently perceive different colors in a video signal. Nine different colors (orange, yellow, red, blue, green, pink, brown, grey, and white) were perceived by the subjects. Different colors can be perceived by the subjects when stimulating the same group of electrodes in the visual prosthesis but with different parameters (e.g., frequency, pulse width, inter-pulse gap, and intra-pulse gap). Current amplitude of the stimulation signal can also be varied, although changes in current amplitude are generally associated with modulation of brightness of a perceived signal and generally do not significantly influence perceived color.

As used in this disclosure, the term "inter-pulse gap" refers to a temporal gap between one biphasic pulse pair and an adjacent biphasic pulse pair whereas "intra-pulse gap" refers to a temporal gap between two opposing stimulation phases (i.e., cathodic and anodic) within a biphasic pulse pair. Since a pulse train of biphasic pulse pairs is generally utilized when stimulating electrodes, the inter-phase gap and the intra-phase gap can both be observed as a temporal gap between cathodic and anodic phases.

For a particular subject and a particular electrode implanted in the particular subject, a set combination of parameters (e.g., frequency, pulse width, inter-pulse gap, and intra-pulse gap) consistently elicits perception of the same color. By way of example, consider that for electrode 1 of subject 'A', the stimulation signal has a pulse frequency, pulse width, and inter-phase gap of 10 Hz, 0.2 ms, and 3 ms, respectively, and elicits perception of the color blue. Consider a different subject (e.g., subject 'B') or a different electrode of subject 'A' with the same stimulation signal (i.e., pulse frequency, pulse width, and inter-phase gap of 10 Hz, 0.2 ms, and 3 ms, respectively). This different subject or different electrode of subject 'A' might or might not elicit perception of the color blue.

Experimentally obtained data is stored for each individual subject and each electrode implanted in each individual subject in a look-up table for use in future simulations. Generally, the experimentally obtained data from the simulation is utilized in future simulations for the particular subject from which the data was obtained. Specifically, the look-up table can store a mapping between stimulation signal parameters and color perceived for a particular electrode of a particular subject. Subsequent video data can be run through the mapping and the color of each image pixel in the video data can be translated (mapped) at each point in time to a stimulation signal for a given electrode at a given point in time. From the mapping, a stimulation signal of a certain frequency, pulse width, inter-pulse gap, and/or intra-pulse gap can be applied to each electrode of each subject to yield perception of an expected and/or desired color at each electrode.

Figure 8:
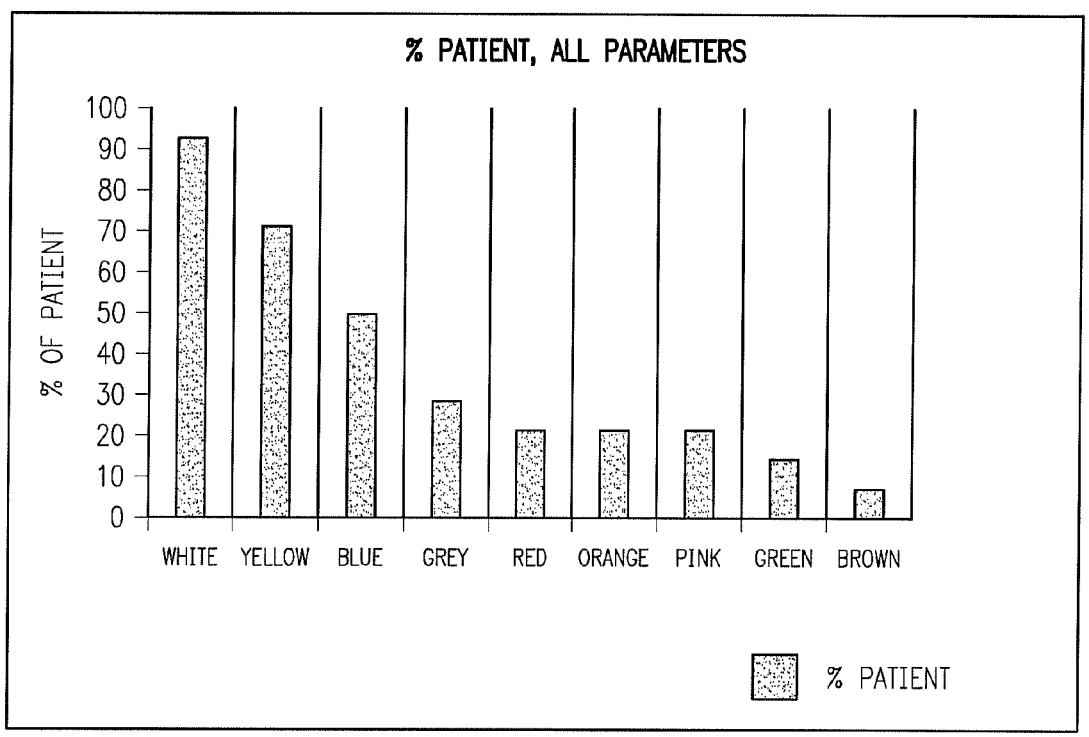
FIG. 8 shows a bar graph depicting percentage of subjects that perceived a particular color.
Figure 9A:
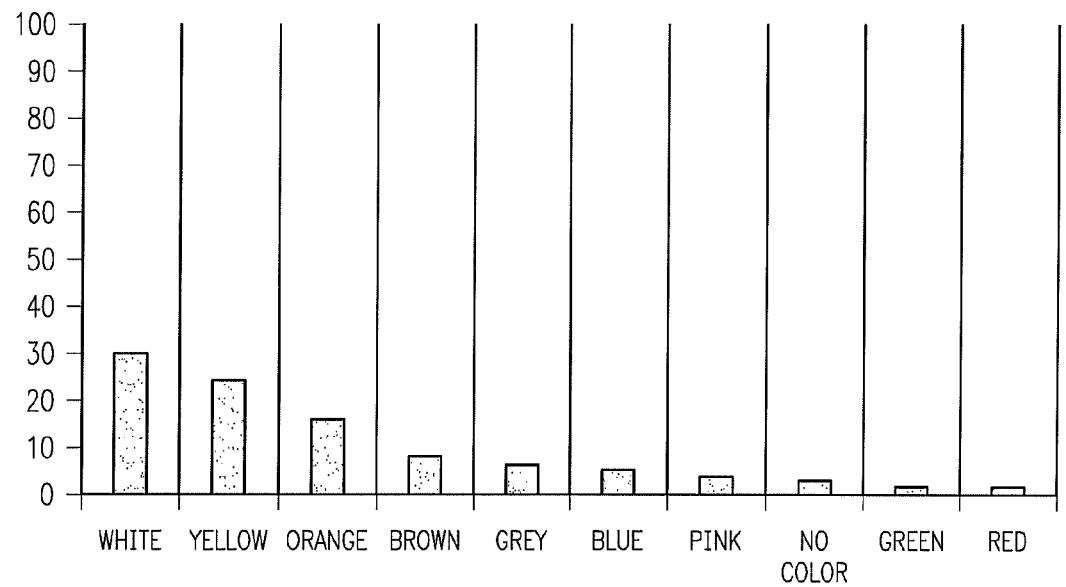
FIG. 9A-9E show bar graphs depicting percentage of subjects that perceived a particular color for different pulse frequencies.
Figure 9B:
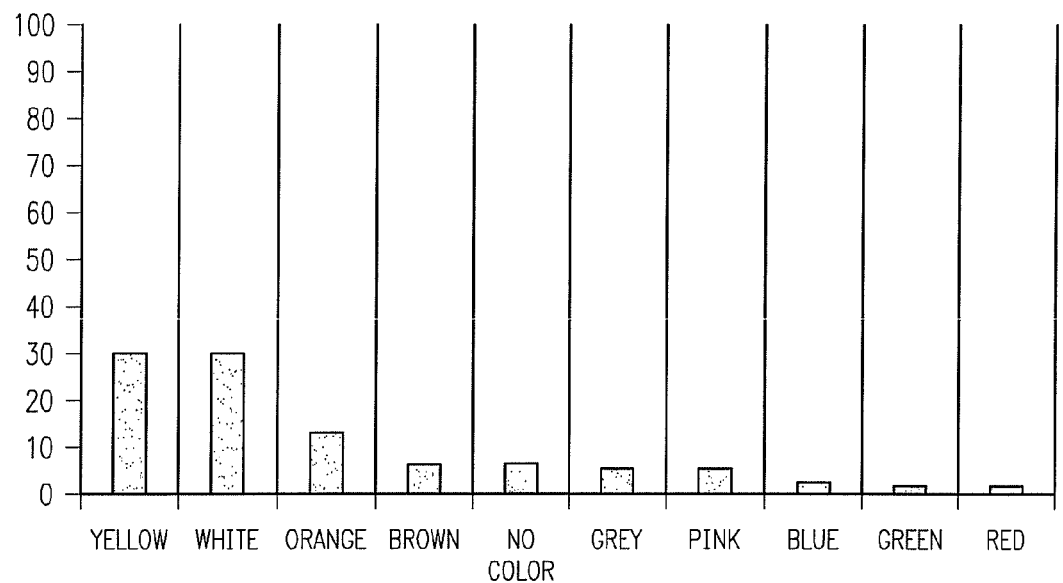
Figure 9C:
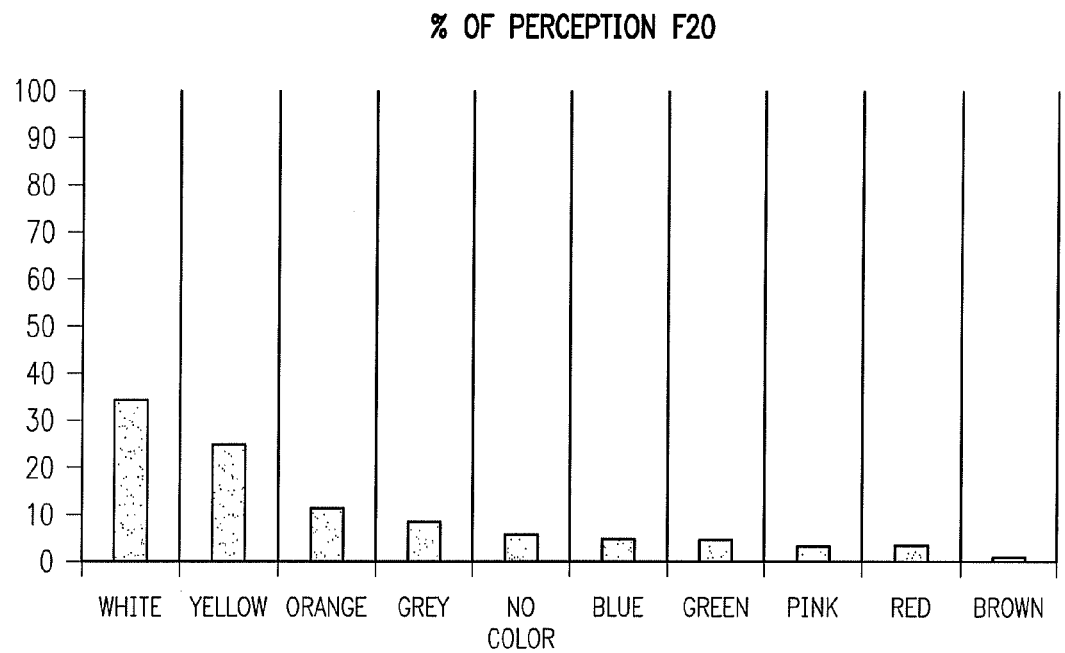
Figure 9D:
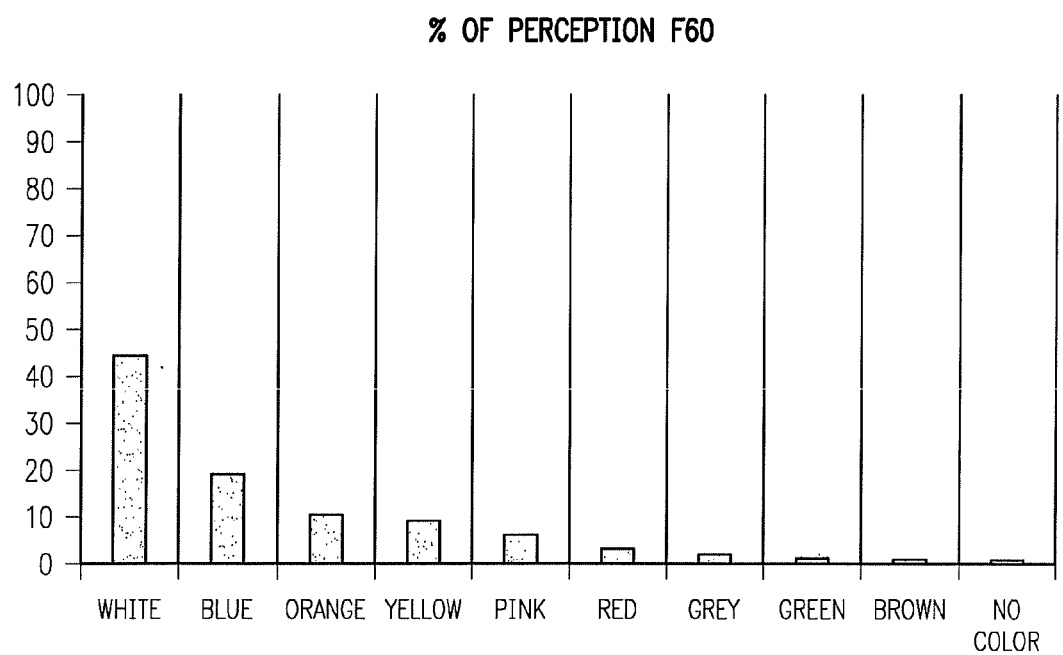
Figure 9E:
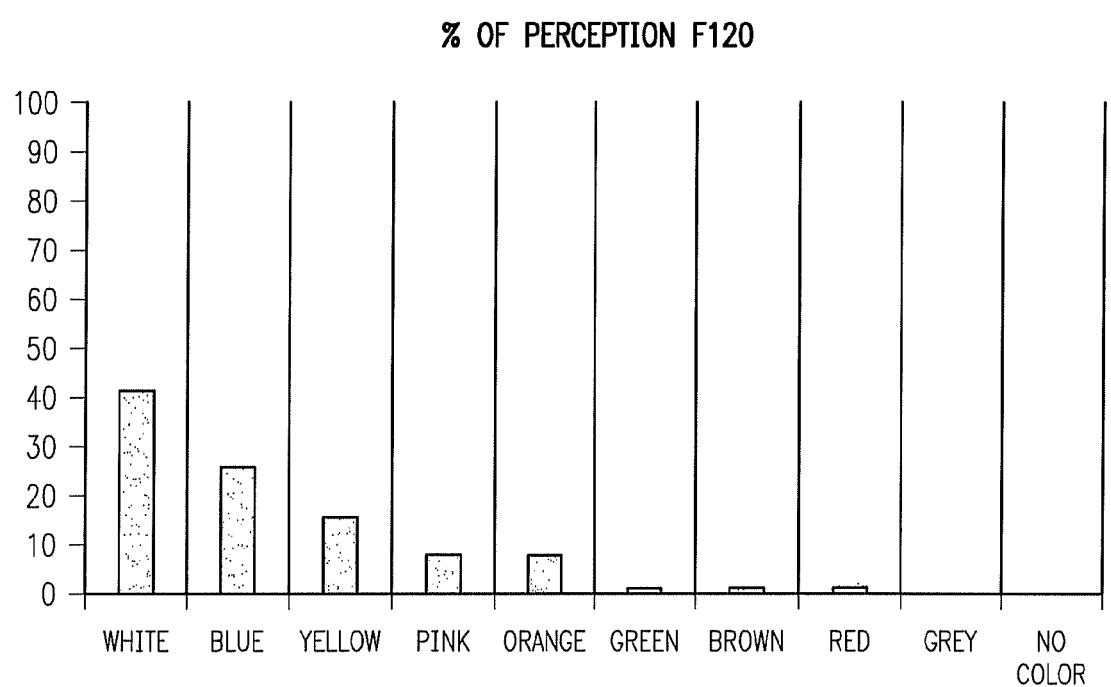
Figure 10A:
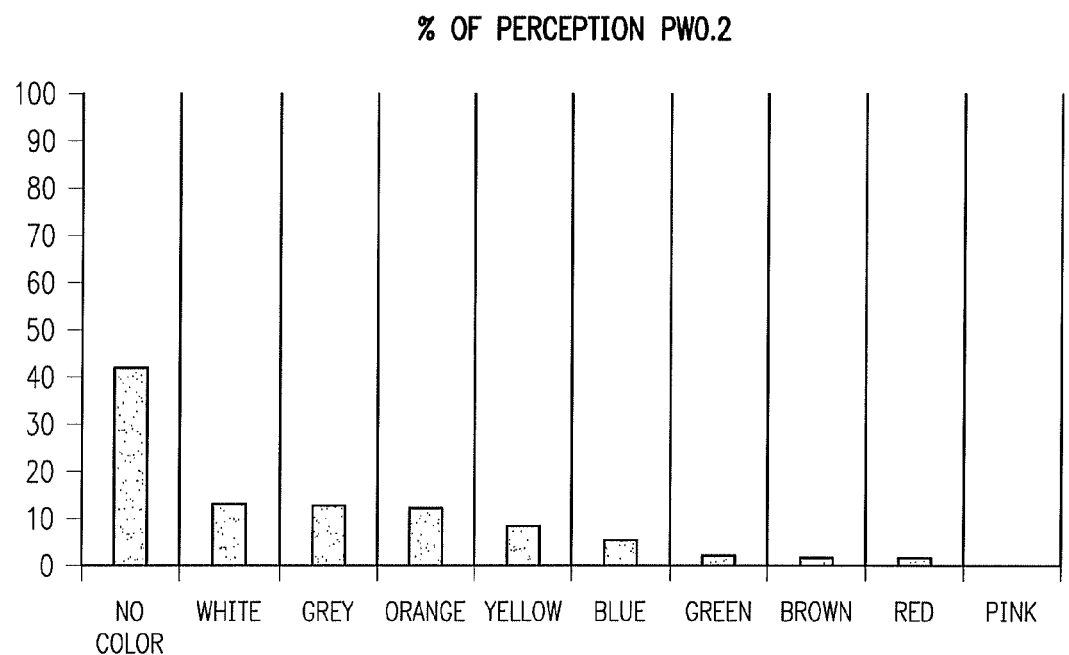
FIGS. 10A-10E show bar graphs depicting percentage of subjects that perceived a particular color for different pulse widths.
Figure 10B:
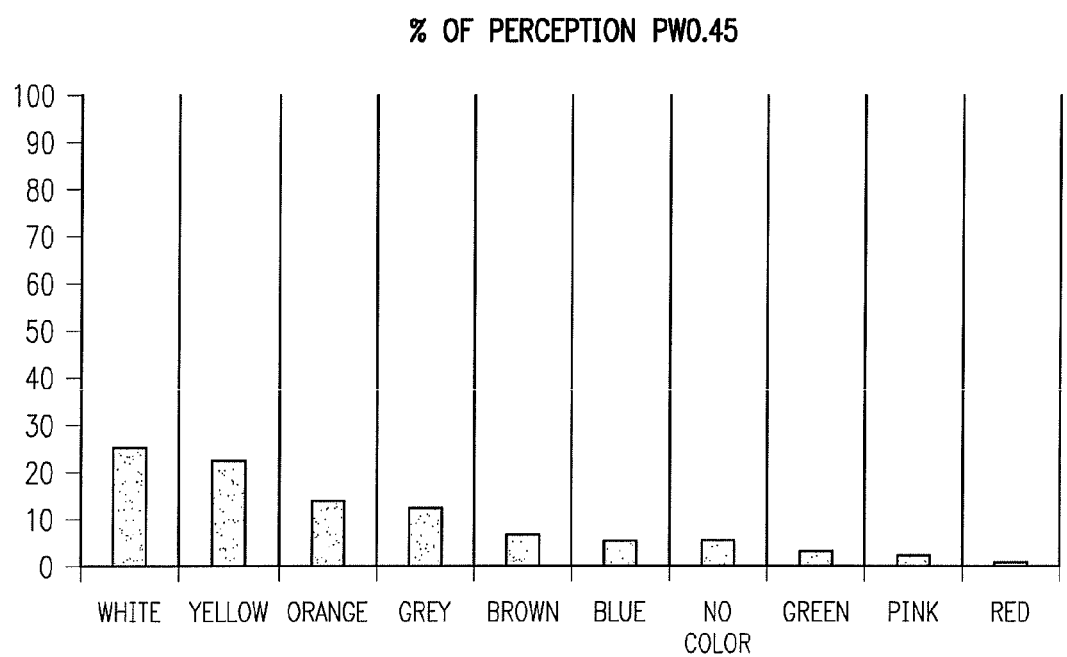
Figure 10C:
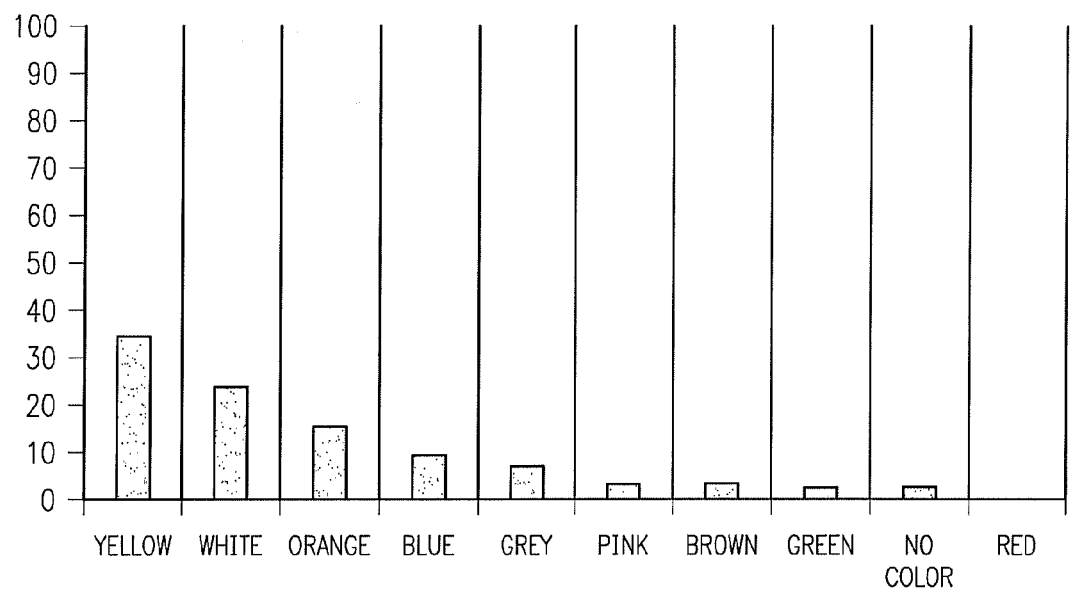
Figure 10D:
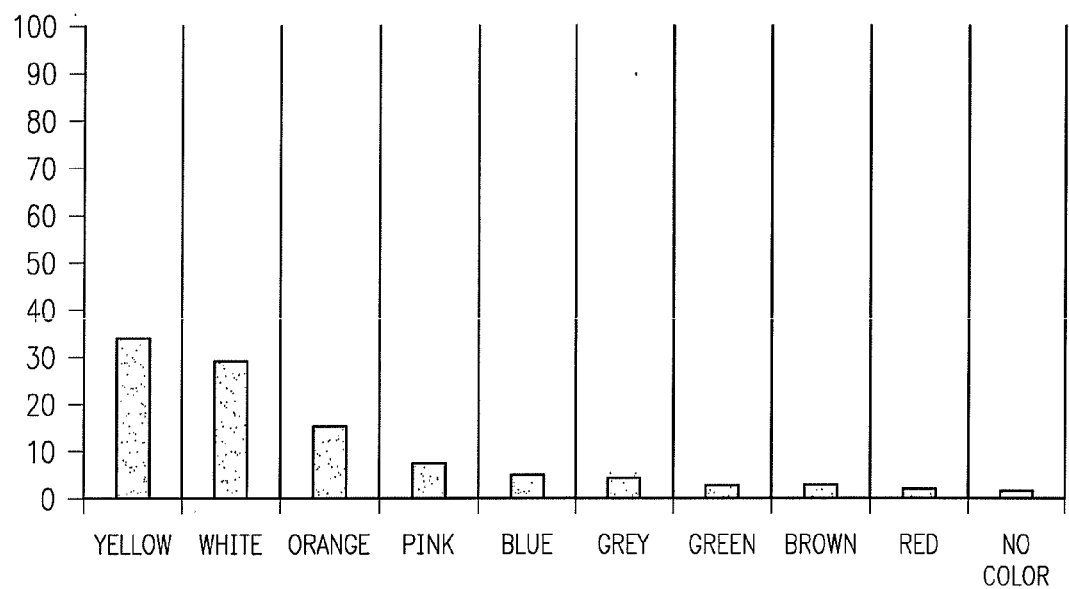
Figure 10E:
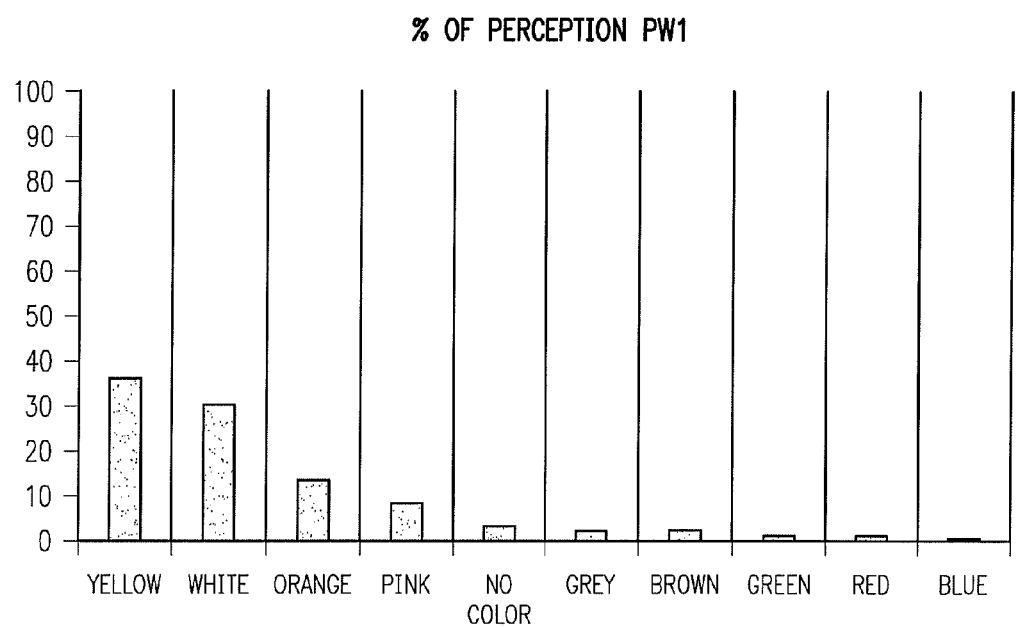
Figure 11A:
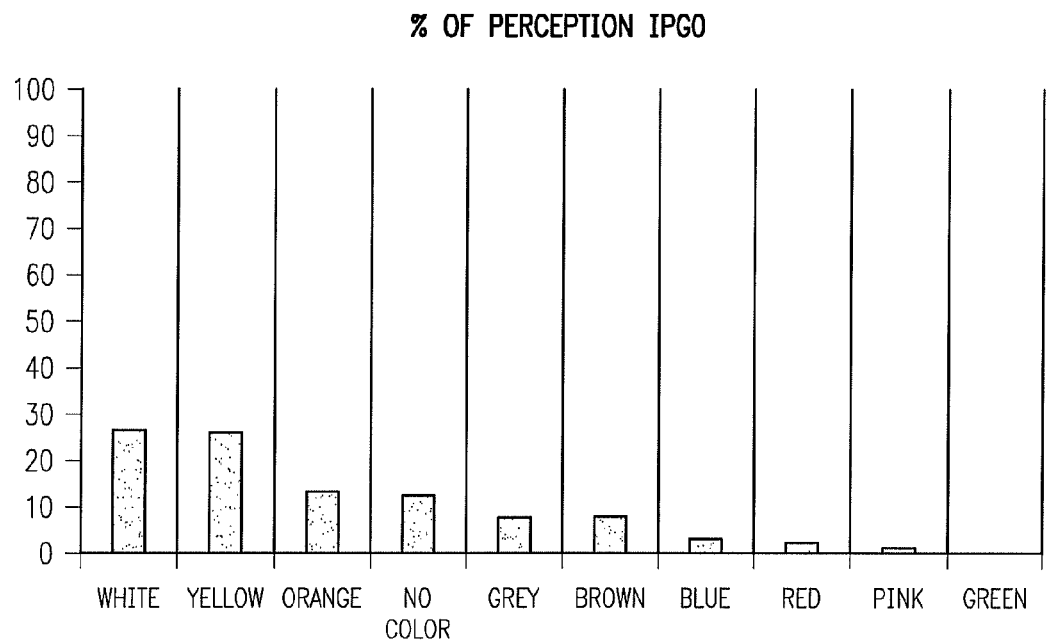
FIGS. 11A-11E show bar graphs depicting percentage of subjects that perceived a particular color for different inter-pulse gaps.
Figure 11B:
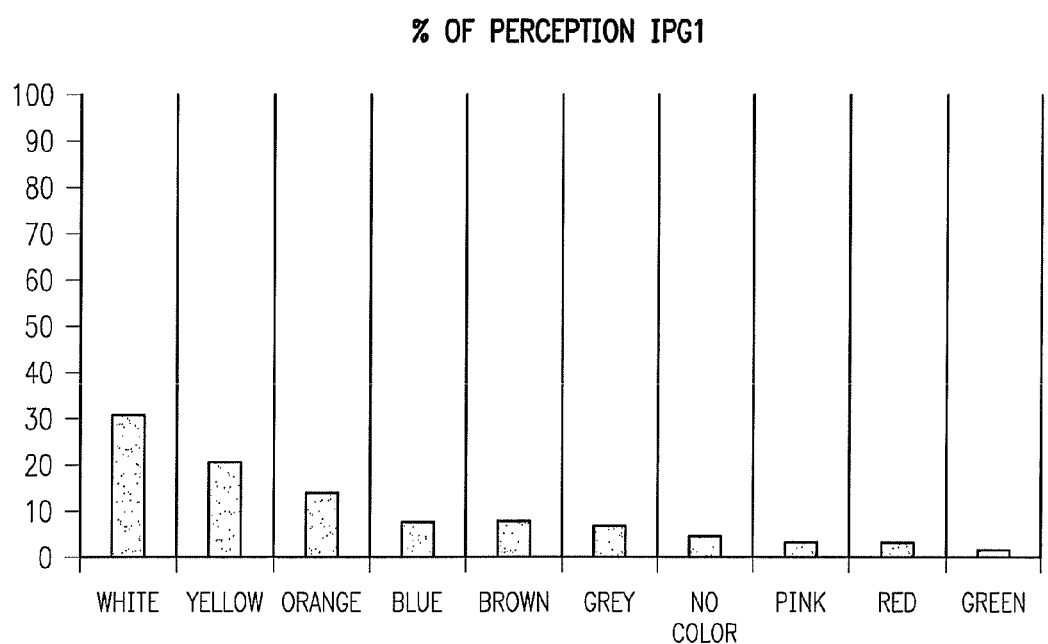
Figure 11C:
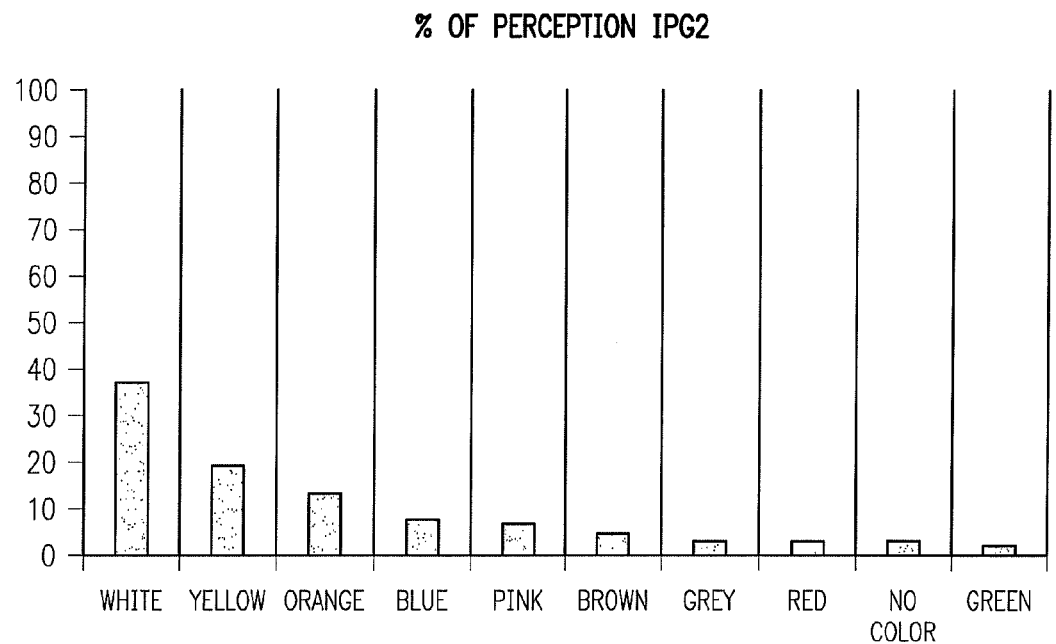
Figure 11D:
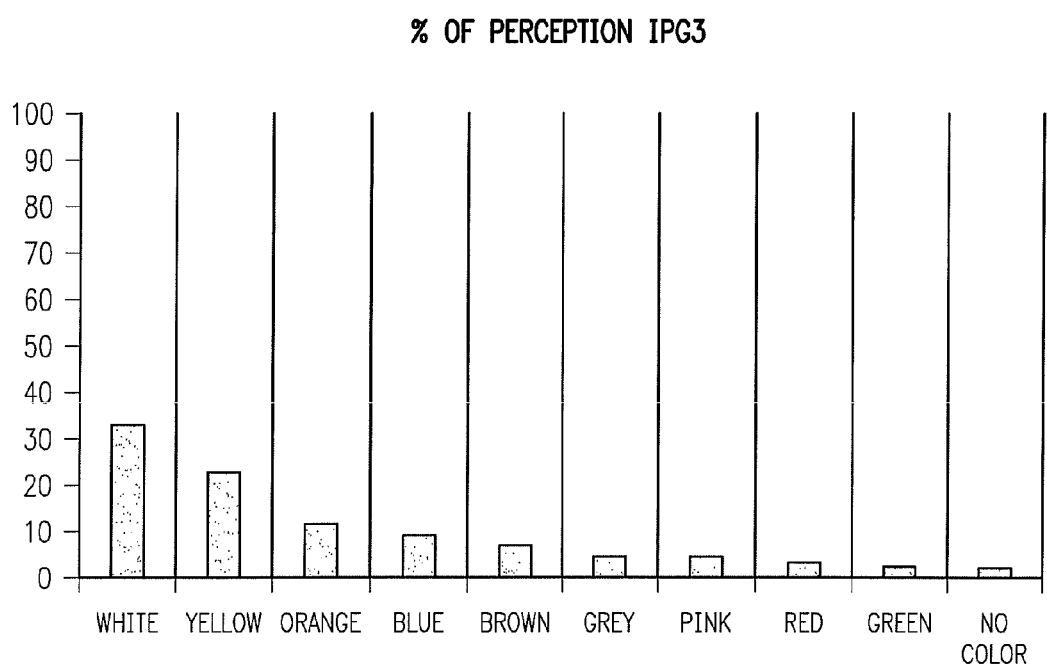
Figure 11E:
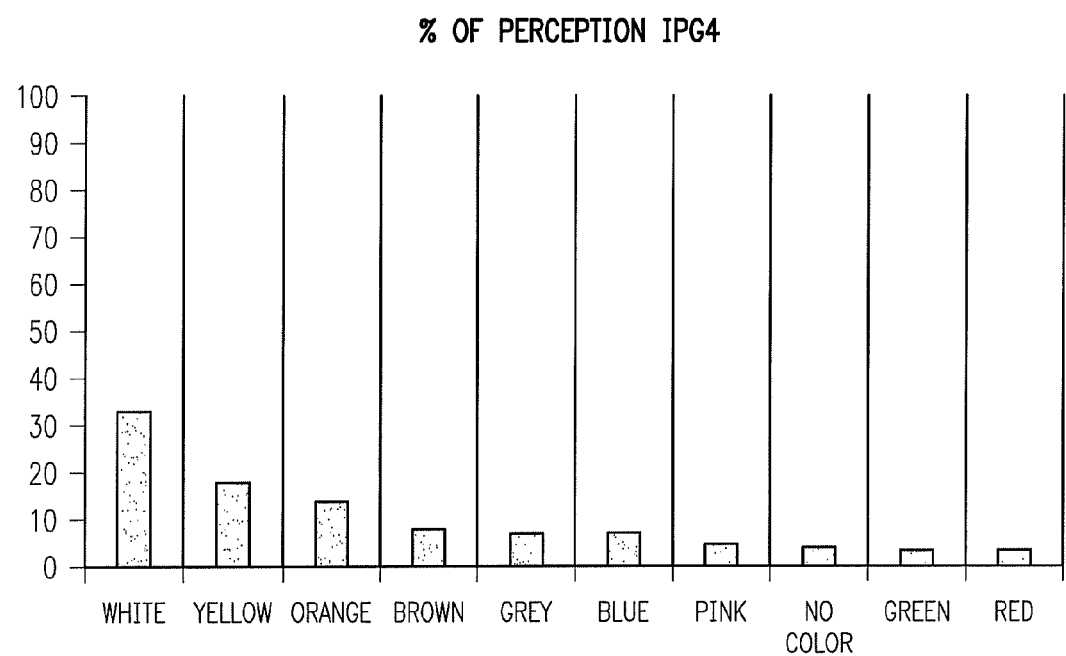

FIG. 8 shows a bar graph depicting percentage of subjects that perceived a particular color. In the experiment, white, yellow, and blue were the predominant colors perceived by the patients. Specifically, FIG. 8 shows that thirteen (around 92%), ten (about 71%), and seven (50%) of the fourteen subjects perceived white, yellow, and blue, respectively, during the experiment. The other colors (grey, red, orange, pink, green, and brown) were perceived rarely.

As shown in FIG. 8 and as will be shown in FIGS. 9A-9E, 10A-10E, and 11A-11E, white and yellow are generally commonly perceived colors regardless of parameters of the stimulation signal. A reason for common perception of the white color is that the white color is perceived through stimulation of each of red, green, and blue cone pathways. Similarly, stimulation of the red and green cone pathways, which are more plentiful than the blue cone pathways, allows perception of yellow. The common perception of the blue color may be a result of a time constant of the red, green, and blue cone pathways, since some experimental data (shown in FIGS. 9A-9E) show more subjects perceiving the blue color when the stimulation signal has a higher frequency.

FIGS. 9A-9E show bar graphs depicting percentage of the subjects that perceived a particular color for different pulse frequencies. Specifically, FIG. 9A-9F show data for pulse frequencies of 5, 10, 20, 60, and 120 Hz, respectively.

FIGS. 10A-10E show bar graphs depicting percentage of the subjects that perceived a particular color for different pulse widths. Specifically, FIGS. 10A-10E show data for pulse widths of 0.2, 0.45, 0.6, 0.8, and 1 ms, respectively.

FIGS. 11A-11E show bar graphs depicting percentage of the subjects that perceived a particular color for different inter-pulse gaps. Specifically, FIGS. 11A-11E show data for inter-phase gaps of 0, 1, 2, 3 and 4 ms, respectively.

From the data collected and shown in FIGS. 9A-9E, percentage of perception of the blue color increased ($p<0.05$) with an increase in pulse frequency, where p refers to the p-value and is a commonly known measure of statistical significance. A very low percentage (less than 5%) of subjects perceived the blue color at 5 Hz and 10 Hz. However, the percentage of subjects that perceived the blue color steadily increased upwards to about 25% at a frequency of 120 Hz. Consequently, as previously mentioned, perception of colors can be a function of a time constant of the red, green, and blue cone pathways. As shown in FIGS. 10A-10E and 11A-11E, no significant change ($p>0.05$) in the blue color was observed by varying the pulse width and the inter-phase gap.

With reference back to FIGS. 9A-9E, percentage of subjects that perceived the yellow color steadily decreased with increasing frequency, which may show that stimulation of the red, green, and blue cone pathways are functions of frequency. Dependency of stimulation on the frequency of the stimulation signal can also be observed in other situations. For example, whereas one would generally utilize lower frequencies to stimulate deeper bipolar cells, higher frequencies would generally be utilized to stimulate more superficial ganglion cells. These observations are described in U.S. Pat. No. 5,944,747, which is incorporated herein by reference in its entirety.

From the data collected and shown in FIG. 10A-10E, an increase in pulse width is associated with an increase in the percentage of perception of the yellow color and a decrease in percentage of perception of the grey color. From the data collected and shown in FIG. 11A-11E, a change in inter-phase gap does not appear to affect percentage of perception of colors in a significant manner.

From the experiments conducted and the results shown in FIGS. 9A-9E, 10A-10E, and 11A-11E, the blind subjects fitted with the retinal prosthesis system were able to perceive different colors through electrical stimulation.

Accordingly, what has been shown is an improved method of controlling color perception in a visual prosthesis. While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein.

It is to be understood that the disclosure is not limited to particular methods or systems, which can, of course, vary. For example, the person skilled in the art will understand that the number steps or components shown is only indicative and that the method can occur in more or fewer steps and that the system may contain more or less components according to the various embodiments. It is also to be understood that the terminology used herein is for the purpose of describing particular embodiments only, and is not intended to be limiting. As used in this specification and the appended claims, the singular forms "a", "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

A number of embodiments of the disclosure have been described. Nevertheless, it will be understood that various modifications may be made without departing from the spirit and scope of the present disclosure. Accordingly, other embodiments are within the scope of the following claims.

What we claim is:

1. A method of inducing perception of color with a visual prosthesis, comprising:
   a. testing a stimulation pattern on a subject on an electrode group or an individual electrode;
   b. determining if a subject perceives a particular color in response to the first stimulation pattern;
   c. altering at least one of frequency, pulse width, inter-pulse gap, and intra-pulse gap in the stimulation pattern based on the step of determining until a desired color perception is obtained;
   d. repeating steps a-c for each electrode or electrode group in an array of electrodes;
   e. storing relationships of each of said electrode groups or individual electrodes to stimulation patterns and colors; and
   d. using the stored relationships to determine patterns used for later stimulation for that subject.

2. The method according to claim 1, wherein the step of testing stimulation patterns includes testing variations in frequency.

3. The method according to claim 1, wherein the step of testing stimulation patterns includes testing variations in pulse width.

4. The method according to claim 1, wherein the step of testing stimulation patterns includes testing variations in inter-pulse gap.

5. The method according to claim 1, wherein the step of testing stimulation patterns includes testing variations in intra-pulse gap.

6. The method according to claim 1, wherein the step of storing relationships comprises storing relationships of stimulation patterns and colors in look-up tables.

7. The method according to claim 1, wherein the step of testing stimulation patterns is performed using an array of electrodes, and wherein a stimulation amplitude of a stimulation signal to be applied to one electrode in the array of electrodes is based on values in the look-up tables.

8. The method according claim 1, wherein the step of testing stimulation patterns is performed using an array of electrodes, and wherein at least one of frequency, pulse width, inter-pulse gap, and intra-pulse gap of a stimulation signal to be applied to one electrode in the array of electrodes is based on values in the look-up tables.

9. The method according to claim 6, wherein each subject is associated with one or more look-up tables specific to each subject.

10. The method according to claim 6, wherein each electrode in the array of electrodes for each subject is associated with one or more look-up tables specific to each subject.

11. A visual prosthesis, comprising:
    a camera providing video data to a video processing unit;
    the video processing unit including memory means for storing individual, color video configuration information including at least one of frequency, pulse width, inter-pulse gap, and intra-pulse gap derived from testing of individual electrodes or electrode groups separately for each of a plurality of electrode groups or individual electrodes, and processing means for altering the video data according to the stored color video configuration information; and
    a neural stimulator receiving video data from the video processing unit and stimulating visual neurons according to video data altered according to the color video configuration information for that subject.

12. The visual prosthesis according to claim 11, wherein the individual color video configuration information is stored in look-up tables.

13. The visual prosthesis according to claim 12, further comprising an array of electrodes adapted to provide stimulation signals to a subject based on the altered video data, wherein a stimulation amplitude of a particular stimulation signal to be applied to one electrode in the array of electrodes is based on values in the look-up tables.

14. The visual prosthesis according to claim 12, further comprising an array of electrodes adapted to provide stimulation signals to a subject based on the altered video data, wherein at least one of frequency, pulse width, inter-pulse gap, and intra-pulse gap of a particular stimulation signal to be applied to one electrode in the array of electrodes is based on values in the look-up tables.

15. The visual prosthesis according to claim 11, further comprising an array of electrodes adapted to provide stimulation signals to a subject, wherein the individual color video configuration information is obtained by applying, for each electrode in the array of electrodes, a particular stimulation signal to one electrode in the array of electrodes and adjusting at least one of frequency, pulse width, inter-pulse gap, and intra-pulse gap of the particular stimulation signal based on feedback from the subject.

* * * * *